United States Patent [19]

Sturm et al.

[11] Patent Number: 4,478,843
[45] Date of Patent: Oct. 23, 1984

[54] 5-PHENYLTETRAZOLES AND THEIR USE AS SALIDIURETICS

[75] Inventors: Karl Sturm, Heidesheim; Roman Muschaweck, Frankfurt am Main; Max Hropot, Flörsheim am Main, all of Fed. Rep. of Germany

[73] Assignee: Hoechst Aktiengesellschaft, Frankfurt am Main, Fed. Rep. of Germany

[21] Appl. No.: 318,153

[22] Filed: Nov. 4, 1981

[30] Foreign Application Priority Data

Nov. 6, 1980 [DE] Fed. Rep. of Germany ....... 3041812

[51] Int. Cl.³ .................. C07D 257/04; A61K 31/41
[52] U.S. Cl. .................................... 424/269; 548/252
[58] Field of Search ........................ 548/252; 424/269

[56] References Cited

U.S. PATENT DOCUMENTS 4,082,851  4/1978  Feit et al. ................... 564/86 X

FOREIGN PATENT DOCUMENTS 310744  10/1973  Austria .
1815922  6/1970  Fed. Rep. of Germany .

OTHER PUBLICATIONS

Elderfield, "Heterocyclic Compounds", vol. 8, Wiley, NY, NY, 1967.

Primary Examiner—Glennon H. Hollrah
Assistant Examiner—D. B. Springer
Attorney, Agent, or Firm—Curtis, Morris & Safford

[57] ABSTRACT

What are disclosed are salidiuretic compounds of the formula

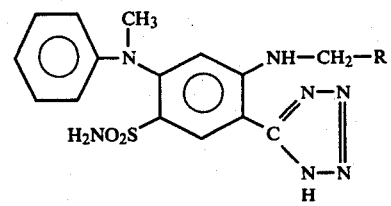

and physiologically acceptable salts thereof, wherein R is phenyl, furyl or thienyl, intermediates of said compounds, methods for making said compounds, salidiuretic pharmaceutical preparations containing said compounds or salts, and methods for treating humans and other mammals with such compounds or salts.

4 Claims, No Drawings

5-PHENYLTETRAZOLES AND THEIR USE AS SALIDIURETICS

The invention relates to compounds of the formula I, which can be assigned to the group comprising the 5-phenyltetrazoles, and to their physiologically acceptable salts.

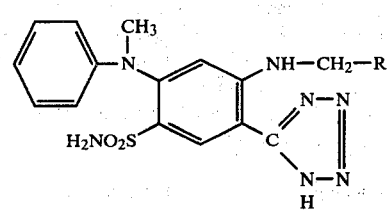

I

In the formula I, R denotes a furyl, thienyl or phenyl radical, preferably the 2-furyl or 2-thienyl radical.

Cations of the salts of compounds of formula I which are suitable for therapeutical use are primarily the sodium, potassium, ammonium and substituted ammonium ions. The salts formed from I and a basic drug, such as antihypertensive agents, β-blockers and potassium-retaining substances, are also of particular importance.

The invention also relates to a process for the preparation of compounds of the formula I, which comprises reacting a compound of the formula II

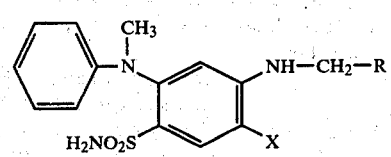

II in which X denotes a nitrile, imidoester, amidine or amidrazone group, with hydrazoic acid or nitrous acid or a reactive derivative of one of these acids.

A preferred industrial process is the reaction of a nitrile (II in which X=CN) with hydrazoic acid. This reaction is carried out by merely heating the reactants in an inert solvent, preferably dimethylformamide. Instead of hydrazoic acid, it is advantageous to use the alkali metal salts, for example sodium azide, which are easier to handle, and to activate these in the reaction mixture by means of a weak acid or a compound having a slightly acid action, such as ammonium chloride.

The reaction of an imidoester or amidine grouping to give the tetrazole can be carried out analogously, while an amidrazone group can be converted into the tetrazole ring by means of nitrous acid or salts thereof.

The nitriles of the general formula III which are preferably used as the starting material can be prepared in a simple manner, for example in accordance with the equation below.

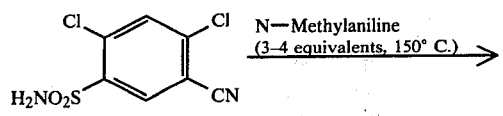

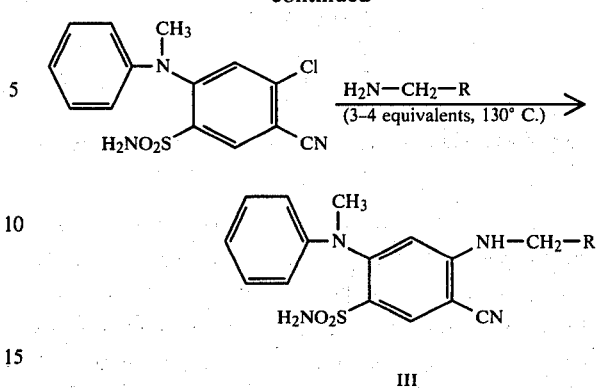

III

The products can be isolated either in the free form or in the form of their salts. It is particularly advantageous to isolate them as sodium or potassium salts, which are only slightly soluble in water at room temperature, but are very readily soluble under hot conditions.

The free tetrazole is preferably converted into an ammonium salt by precipitating the free tetrazole from an aqueous solution of an alkali metal salt with dilute hydrochloric acid at pH 3, and then combining it with an equimolar quantity of the desired amine in a suitable solvent.

The salts of the compounds according to the invention with basic potassium-retaining compounds, such as, for example, amiloride or triamterene, or with basic anti-hypertensive agents, such as, for example, clonidine or dihydralazine, or with β-blockers, are of particular pharmacological importance.

In these compounds the potassium-retaining compounds, antihypertensive agents and β-blockers respectively retain their pharmacological effect and, thus, the salts show a combined effect of both components.

The compounds according to the invention are excellent salidiuretics of the furosemide type. Compared with the salidiuretics having a tetrazole structure which are described in German Pat. No. 1,815,922, they are distinguished by a substantially higher potency, better absorbability and a uricosuric activity.

The compounds according to the invention serve for treating cardiac, renal or hepatic edemas, ascites, edemas of pregnancy, edemas after burns, after venous deficiencies or after thromboses, furthermore for treating low to medium degree hypertension.

They are administered to mammals and to human beings preferably orally or intravenously, the dosage unit of pure active substance being from 1 to 50 mg.

For oral administration, the active compounds are used either in pure form or in a suitable administration form such as tablets, dragées or snap-fit capsules, in admixture with usual additives such as carriers, stabilizers or inert diluents. As inert carriers, magnesium carbonate, lactose or corn starch may for example be used. The formulation may have the form of dry or moist granules.

For intravenous administration, the active compounds, preferably in the form of their physiologically tolerable alkali metal or ammonium salts, are dissolved together with the usual additives. A suitable solvent is preferably water, optionally with addition of known buffer substances, solubilizers and stabilizers.

EXAMPLES

Example 1

Sodium 5-[2-furfurylamino-4-(N-methylanilino)-5-sulfamoylphenyl]-tetrazole 38.3 g (0.1 mole) of 2-furfurylamino-4-(N-methylanilino)-5-sulfamoylbenzonitrile, melting point 205° C. (from methanol), were stirred, together with 13.0 g of sodium azide and 11.0 g of ammonium chloride, in 0.6 l of dimethylformamide for 3 hours at 110° C. The dimethylformamide was then removed in vacuo and the residue from evaporation was taken up in 0.3 l of 1N NaOH. The solution was decolorized with active charcoal and its pH was then adjusted to 8.0 with 2N HCl. After standing overnight at 10° C., the precipitate was filtered off and the end product was recrystallized again from water. After being washed with isopropanol it was dried at 100° C.

Yield: 36.5 g (81% of theory), melting point 221° C. (with decomposition)

Example 2

Sodium 5-[2-thienylmethylamino)-4-(N-methylanilino)-5-sulfamoylphenyl]-tetrazole 39.9 g (0.1 mole) of 2-(2-thienylmethylamino)-4-(N-methylanilino)-5-sulfamoylbenzonitrile, melting point 182° C. (from methanol), were subjected to a condensation reaction with $HN_3$ analogously to Example 1 and the end product was isolated as described in that Example.

Yield: 38.5 g (83% of theory), melting point 216° C. (with decomposition).

Example 3

Sodium 5-[2-benzylamino-4-(N-methylanilino)-5-sulfamoylphenyl]-tetrazole 39.3 g (0.1 mole) of 2-benzylamino-4-(N-methylanilino)-5-sulfamoylbenzonitrile, melting point 162° C. (from methanol), were subjected to a condensation reaction with $HN_3$ analogously to Example 1 and, after removing the dimethylformamide, the residue was recrystallized from 1N $NaHCO_3$, with the addition of active charcoal. After being washed with water, the product was dried at 100° C.

Yield: 36 g (63% of theory), melting point 208° C. (with decomposition).

We claim:

1. A 5-phenyltetrazole of the formula

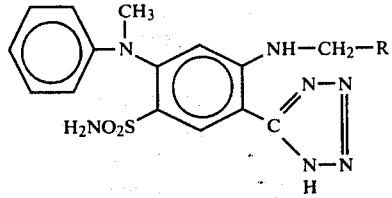

wherein R is phenyl, 2-furyl, or 2-thienyl, or a physiologically acceptable salt thereof formed with a base.

2. A salidiuretic pharmaceutical preparation for the treatment of edema and hypertension, said preparation comprising a salidiuretically-effective amount of a compound or salt as in claim 1 and a pharmaceutically acceptable carrier therefor.

3. A method for treating edema in a patient suffering therefrom, which method comprises orally or intravenously administering to said patient a salidiuretically-effective amount of a compound or salt as in claim 1.

4. A method for treating hypertension in a patient suffering therefrom, which method comprises orally or intravenously administering to said patient a salidiuretically-effective amount of a compound or salt as in claim 1.

* * * * *